US012594134B2

(12) United States Patent
Maratt

(10) Patent No.: US 12,594,134 B2
(45) Date of Patent: *Apr. 7, 2026

(54) KINEMATICALLY ALIGNED ROBOTIC TOTAL KNEE ARTHROPLASTY

(71) Applicant: Zimmer, Inc., Warsaw, IN (US)

(72) Inventor: Joseph Maratt, Ann Arbor, MI (US)

(73) Assignee: Zimmer, Inc., Warsaw, IN (US)

( * ) Notice: Subject to any disclaimer, the term of this patent is extended or adjusted under 35 U.S.C. 154(b) by 26 days.

This patent is subject to a terminal disclaimer.

(21) Appl. No.: 18/236,130

(22) Filed: Aug. 21, 2023

(65) Prior Publication Data

US 2023/0390004 A1     Dec. 7, 2023

Related U.S. Application Data

(63) Continuation of application No. 16/570,091, filed on Sep. 13, 2019, now Pat. No. 11,766,300.

(Continued)

(51) Int. Cl.
| | |
|---|---|
| *A61B 34/30* | (2016.01) |
| *A61B 17/16* | (2006.01) |
| *A61B 34/10* | (2016.01) |
| *A61B 90/00* | (2016.01) |
| *A61F 2/46* | (2006.01) |
| *G06N 20/00* | (2019.01) |
| *G16H 20/40* | (2018.01) |

(52) U.S. Cl.
CPC .......... *A61B 34/30* (2016.02); *A61B 17/1675* (2013.01); *A61F 2/461* (2013.01); *G06N 20/00* (2019.01); *G16H 20/40* (2018.01); *A61B 2034/105* (2016.02); *A61B 2034/107*

(2016.02); *A61B 2090/367* (2016.02); *A61F 2002/4633* (2013.01); *A61F 2002/4658* (2013.01)

(58) Field of Classification Search
CPC ................ A61B 34/30; A61B 17/1675; A61B 2034/105; A61B 2034/107; A61B 2090/367; G16H 20/40; A61F 2/461; A61F 2002/4633; A61F 2002/4658
See application file for complete search history.

(56) References Cited

U.S. PATENT DOCUMENTS

| | | |
|---|---|---|
| 5,880,976 A | 3/1999 | DiGioia III et al. |
| 9,665,686 B2 | 5/2017 | Van Vorhis et al. |

(Continued)

OTHER PUBLICATIONS

U.S. Appl. No. 16/570,091, filed Sep. 13, 2019, Kinematically Aligned Robotic Total Knee Arthroplasty.

(Continued)

*Primary Examiner* — Zade Coley
*Assistant Examiner* — Diana Jones
(74) *Attorney, Agent, or Firm* — SCHWEGMAN LUNDBERG & WOESSNER, P.A.

(57) ABSTRACT

A system and method may use a robotic arm to perform a range of motion test for use in generating information related to kinematic alignment in a total or partial knee arthroplasty. A method may include controlling a robotic arm to move a tibia throughout a range of motion for a knee. A series of measurements of gap distance for the knee may be used to determine a tibial resection location for the tibia. The method may include updating a plan (e.g., 3D, preoperative) for an orthopedic procedure on the knee with the tibial resection location.

20 Claims, 9 Drawing Sheets

1. 3D PLAN ON ROSA KNEE

2. CUT OSTEOPHYTES FROM TIBIA (HIGH PROVISIONAL CUT)

3. RANGE OF MOTION TEST TO GENERATE AN AXIS THROUGH THE DISTAL FEMUR

4. FEMORAL CUT

5. ADJUST 3D PLAN TO DETERMINE LOCATION OF TIBIAL COMPONENT BASED ON OPTIMIZATION AND RANGE OF MOTION; DETERMINE FINAL TIBIAL CUT

Related U.S. Application Data

(60) Provisional application No. 62/731,471, filed on Sep. 14, 2018.

(56) References Cited

U.S. PATENT DOCUMENTS

| | | | | | |
|---|---|---|---|---|---|
| 9,901,463 | B2 | | 2/2018 | Mahfouz | |
| 11,129,681 | B2 | * | 9/2021 | Amiot | G01B 11/25 |
| 11,291,437 | B2 | * | 4/2022 | Trabish | A61F 2/461 |
| 2012/0209394 | A1 | * | 8/2012 | Bojarski | A61F 2/4202 |
| | | | | | 623/18.11 |
| 2014/0282194 | A1 | * | 9/2014 | Nikou | A61B 34/10 |
| | | | | | 715/771 |
| 2018/0132949 | A1 | * | 5/2018 | Merette | G06T 11/60 |
| 2020/0085517 | A1 | | 3/2020 | Maratt | |

OTHER PUBLICATIONS

"U.S. Appl. No. 16/570,091, Examiner Interview Summary mailed Jan. 19, 2023", 2 pgs.

"U.S. Appl. No. 16/570,091, Examiner Interview Summary mailed Sep. 29, 2022", 2 pgs.

"U.S. Appl. No. 16/570,091, Non Final Office Action mailed Nov. 25, 2022", 8 pgs.

"U.S. Appl. No. 16/570,091, Notice of Allowance mailed May 22, 2023", 8 pgs.

"U.S. Appl. No. 16/570,091, Response filed Feb. 24, 2023 to non Final Office Action mailed Nov. 25, 2022", 8 pgs.

"U.S. Appl. No. 16/570,091, Response filed Oct. 3, 2022 to Restriction Requirement mailed Aug. 3, 2022", 9 pgs.

"U.S. Appl. No. 16/570,091, Restriction Requirement mailed Aug. 3, 2022", 9 pgs.

* cited by examiner 1. 3D PLAN ON ROSA KNEE

2. CUT OSTEOPHYTES FROM TIBIA
(HIGH PROVISIONAL CUT)

3. RANGE OF MOTION TEST TO
GENERATE AN AXIS THROUGH
THE DISTAL FEMUR

4. FEMORAL CUT

5. ADJUST 3D PLAN TO DETERMINE
LOCATION OF TIBIAL COMPONENT
BASED ON OPTIMIZATION AND
RANGE OF MOTION;
DETERMINE FINAL TIBIAL CUT

600

602 —

ROBOTIC SURGICAL ARM

604 —

SENSOR

614 —

DISPLAY DEVICE

616 —

USER INTERFACE

618 —

CONTROL SYSTEM

620 —

PROCESSOR

622 —

MEMORY

KINEMATICALLY ALIGNED ROBOTIC TOTAL KNEE ARTHROPLASTY

CLAIM OF PRIORITY

This application is a continuation of U.S. patent application Ser. No. 16/570,091, filed Sep. 13, 2019, which claims the benefit of priority to U.S. Provisional Application No. 62/731,471, filed Sep. 14, 2018, titled "KINEMATICALLY ALIGNED ROBOTIC TOTAL KNEE ARTHROPLASTY" each of which is hereby incorporated herein by reference in its entirety.

BACKGROUND

Computer-assisted surgery has been developed in order to help a surgeon in altering bones, and in positioning and orienting implants to a desired location. Computer-assisted surgery may encompass a wide range of devices, including surgical navigation, pre-operative planning, and various robotic devices. One area where computer-assisted surgery has potential is in orthopedic joint repair or replacement surgeries. For example, soft tissue balancing is an important factor in joint replacement, as an unbalance may result in joint instability. However, when performing orthopedic surgery on joints, soft tissue evaluations are conventionally done by hand, with the surgeon qualitatively assessing the limits of patient's range of motion. The conventional technique may result in errors or lack precision.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
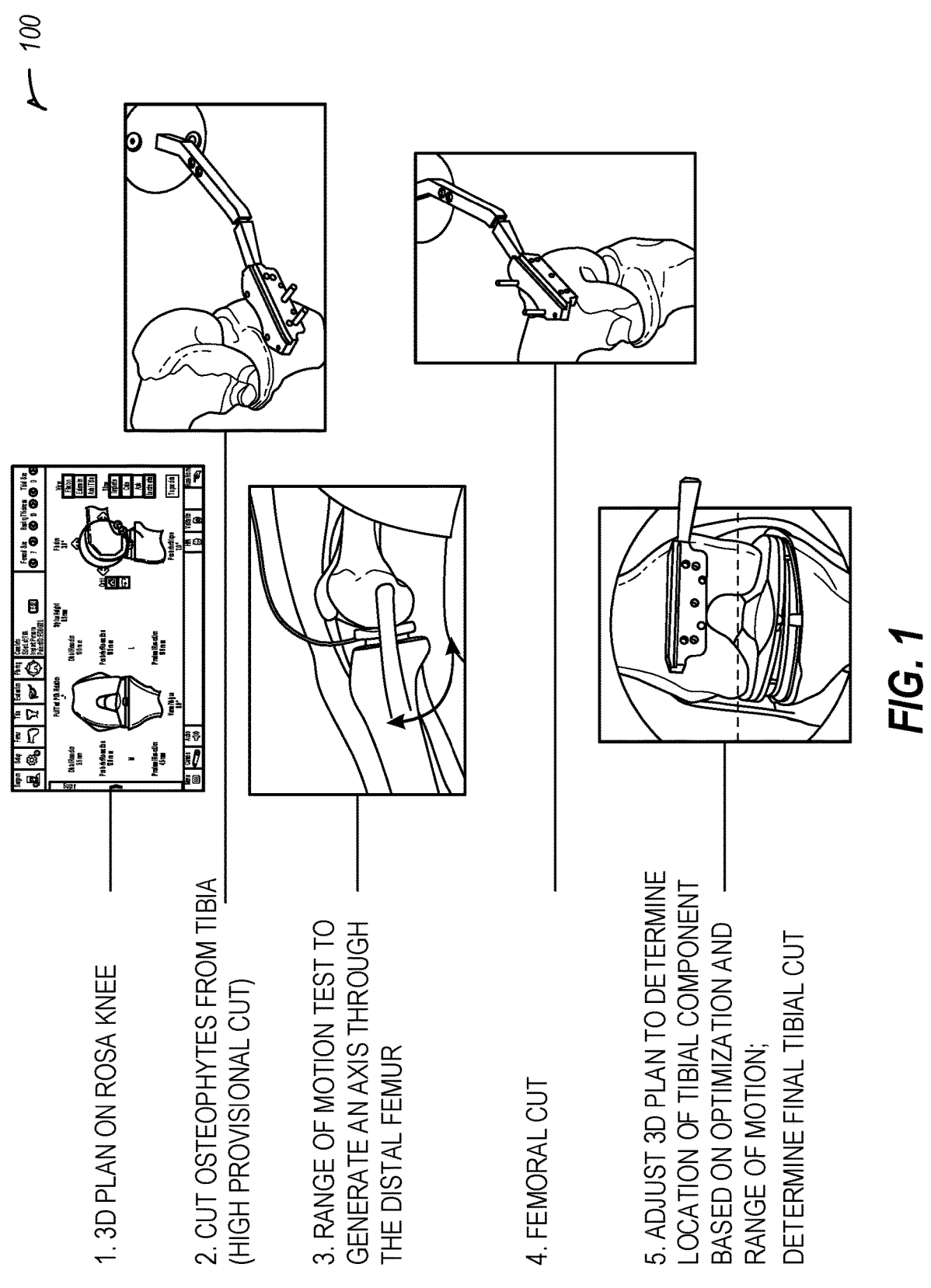
FIG. 1 illustrates a surgical technique in accordance with some embodiments.

Systems and methods for performing kinematic alignment in robotic knee arthroplasty are provided herein. Kinematic alignment is a surgical technique that is used to attempt to restore a native alignment of a knee (e.g., to when the knee was healthy) when performing a knee arthroplasty. In kinematic alignment, ligament releases are minimized and osteophytes are removed. Additional consideration may be made for a proximal tibia cut to balance medial and lateral gaps of the knee. Attention to the thickness of the resected femoral bone compared to implant thickness in a knee arthroplasty aids in kinematic alignment. In an example, a native laxity may be used to determine when a kinematic alignment occurs, the native laxity including a varus/valgus comparison and/or an internal/external knee rotation comparison. Making the varus/valgus angle or internal/external rotation equal may result in kinematic alignment. Reducing ligament releases (e.g., of the posterior cruciate (PCL), collateral (LCL or MCL), or retinacular ligaments) may result in improved outcomes for patients, such as reduced pain or decreased notice of the post-surgical knee.

In an example, evaluating kinematic alignment may include performing a range of motion test. The range of motion test may be used to evaluate angles, gap distance, or other aspects of soft tissue. Some techniques for evaluating kinematic alignment may rely on imprecise measurements, such as surgeon estimates, hand performed techniques, or other have qualitative properties. These techniques may be limited in accuracy for kinematic alignment.

Robotics offer a useful tool for assisting the surgeon in the surgical field. A robotic device may assist in the surgical field performing tasks such as biopsies, electrode implantation for functional procedures (e.g., stimulation of the cerebral cortex, deep brain stimulation), open skull surgical procedures, endoscopic interventions, other "key-hole" procedures, arthroplasty procedures, such as total or partial knee replacement, hip replacement, shoulder implant procedures, or the like. In an example, a surgical procedure may use a surgical robot. The surgical robot may include a robotic arm for performing operations. A tracking system may be used to determine a relative location of the surgical robot or robotic arm within a coordinate system or a surgical field. The surgical robot may have a different coordinate system or tracking system (e.g., using known movements of the surgical robot). The robotic arm may include an end effector of the robotic arm of the surgical robot, which may use sensors, such as a gyroscope, magnetoscope, accelerometer, etc. In an example, a processor may be used to process information, such as tracking information, operation parameters, applied force, location, or the like.

A robotic system including a robotic arm, controlled using a robotic controller with precise location sensing and force actuation may be used to evaluate aspects of a knee to determine kinematic alignment in the knee. For example, the robotic system may be used to perform a range of motion test. The robotic system may include a sensor, such as an accelerometer, a gyroscope, or the like for evaluating position, speed, or acceleration of the robotic arm. In an example, an optical tracking system may be used with the robotic system to determine location of aspects of the robotic system or a patient. The robotic system may include force actuation components (e.g., a motor) to control the robotic arm, and a force sensor for determine an amount of force applied on or by the robotic arm.

A range of motion test may be performed using a robotic arm to move a patient's tibia through a range of motion, and a robotic system or a tracking system (when separate from the robotic system, for example an optical tracking system) may be used to track gap distance within the knee of the patient, varus/valgus angle, or other aspects of soft tissue or alignment of the knee. Determining kinematic alignment using a robotic arm to perform a range of motion test is described further herein below. Using the robotic arm allows for objective analysis of kinematic alignment through a range of motion test. The precision of location information obtained by the robotic arm may be used during the range of motion test to determine kinematic alignment of a patient's knee throughout the range of motion. The location information may be used to modify or generate a 3D plan for a surgical knee procedure. The location information obtained by the robotic arm may include more data points or be more precise than previous techniques (e.g., a surgeon visual inspection).

FIG. 1 illustrates a surgical technique 100 in accordance with some embodiments. The technique 100 includes an operation to develop a 3D plan for a knee procedure. The 3D plan may include a robotic component, such as using a robotic arm to: move a patient limb (e.g., lower leg, tibia, etc.) through a range of motion, hold a cut guide, make a resection, or the like. The 3D plan may include a proposed implant, trial, gap distance (which may differ medially and laterally), a proposed resection location (e.g., for a femur or tibia), or other aspects of a knee arthroplasty.

The technique 100 may include performing a cut of an osteophyte from the tibia. The cuts may be performed by a surgeon, by the robotic arm autonomously, or by the surgeon and the robotic arm in a cooperative mode (e.g., with a force assist). After the osteophytes are removed with a high provisional cut of the tibia, a range of motion test may be performed.

The technique 100 includes performing a range of motion test to generate information about the knee, such as gap distance within the knee of the patient, a varus/valgus angle, other aspects of soft tissue or alignment of the knee, an axis through the distal femur, a position of a femoral component, a tibial cut location, a shape of an implant, or the like. The range of motion test in technique 100 is performed by the robotic arm, moving the knee (e.g., moving the tibia, while the femur is kept static) through the range of motion. The robotic arm may perform the range of motion movement entirely autonomously (e.g., without surgeon input after, for example, an initial indication to start the movement) or as a force assist or stabilization force (e.g., according to a surgeon's speed indication, for example by gently pushing on the robotic arm, the robotic arm may retain an angle or direction of motion, but move according to a speed input by the surgeon).

In an example, measurements may be obtained at one or more points along the range of motion. For example, measurements may be taken at degree, half degree, quarter degree or at another frequency increments along a range of motion. In an example, measurements may be taken at uniform intervals along the range of motion (e.g., from flexion to extension) or may be taken at arbitrary intervals. The measurements may be obtained using an optical tracking system (e.g., an optical tracker on the tibia, optionally on the femur, and an optical camera or sensing device, such as an infrared camera may be used to obtain location information about the optical tracker, which may be used to determine gap distance, varus/valgus angle, etc.). In an example, a sensor of the robotic arm system may be used. For example, an accelerometer, a gyroscope, a position sensor, or other location sensor, a force or torque sensor, or the like may be used to obtain information about the knee or the robotic arm system. In an example, measurements may be taken by a device coupled to anatomy of the patient (e.g., a wearable device strapped to the patient's ankle). Measurements may be used to evaluate the 3D plan and to update the plan. Updates may be suggested to the surgeon or may be applied to the 3D plan automatically.

The technique 100 may include performing a femoral cut (e.g., the surgeon may make the cut, the robotic arm may make the cut autonomously, or the surgeon may use a force assist from the robotic arm to perform the cut).

The technique 100 includes adjusting or updating the 3D plan to determine a location of a tibial component, such as based on optimization and the range of motion (e.g., measurements taken during the range of motion movement). The technique 100 may include determining a final tibial cut to be performed. The final tibial cut may be based on the measurements or the update to the plan. For example, the update to the 3D plan may include a change in determined gap distance from the measurement data, resulting in a recommendation or automatic change to a corresponding trial or implant. In an example, a new implant may result in a change in tibial cut location or a change in femoral cut location.

In an example, measurements, data, the 3D plan, or other patient-specific information may be used to generate an adjustment to the plan. For example, laxity may be reduced by increasing a trial or implant size or by changing a location of a tibial cut.

In an example, the technique 100 may use a robotic arm with specified capabilities or controlled to function in a particular manner. For example, the robotic arm may be controlled to provide position sensing. In this example, the robotic arm may be affixed to patient anatomy (e.g., the tibia or the ankle) and output position information. The robotic arm may, in this example, not apply any force while tracking position changes of the anatomy (and measurements may be output, such as from the robotic arm or an optical tracking system). The surgeon in this example may apply the force and control movement throughout the range of motion.

In another example, the robotic arm may be controlled to provide position sensing and force assistance, such as with stabilization. In this example, the robotic arm may aid the surgeon in moving the anatomy throughout the range of motion. For example the robotic arm may provide force assistance (e.g., when the surgeon begins to move or indicates to move the anatomy or the robotic arm, the robotic arm may amplify the surgeon's force or provide force from an indication to move the anatomy). In this example, whether the force assist is provided or not, the robotic arm may provide stabilization (e.g., by keeping the anatomy within a selected plane of movement).

In yet another example, the robotic arm may perform all or portions of the range of motion movement autonomously. For example, the surgeon may input a speed or initialize the robotic arm, after which the robotic arm may move the patient anatomy throughout the range of motion, providing force, stabilization, and position sensing. In another example of autonomous movement of the robotic arm, the surgeon may provide an input (e.g., on a user interface, with a controller such as a joystick or switch, or the like) indicating a movement direction, speed, start/stop, or other control to which the robotic arm may respond. This movement is considered autonomous in that the surgeon does not need to directly touch the patient or the robotic arm to perform the range of motion movement.

In an example, based on movement of patient knee anatomy throughout a range of motion, cartilage losses in the knee may be estimated using a model of the knee from the 3D plan. As the anatomy of the knee is moved through the range of motion, an axis through the distal femur may be generated. The axis may be used to determine how a femoral component is to be positioned. Based on the axis and the mapped cartilage at the end of the femur, tolerance levels may be determined. The tolerance may be used to decide where to place the femoral component to minimize deviation from a native knee. A minimization operation may be used to find a lowest error between the femoral implant and the cartilage of the distal femur.

After a location for the placement of the femoral component is determined, the tibial cut location may be determined. As the knee goes through the range of motion, a model of a shape of an implant may be determined along the range of motion as the knee articulates with the femur. The tibial cut may be determined such that gaps between the femur and tibia are minimized throughout the range of motion. In an example, a threshold maximum gap may be used, or in another example, a minimum average or overall gap may be used throughout the range of motion. In an example, the implant may be optimized with different gap sizes (e.g., 1 mm on medial, 2 mm on lateral for example, or 1 mm at extension, and 1 mm medial and 2 mm lateral at flexion).

In an example, an expandable trial may be used. The expandable trial may be inserted into the knee after a cut is made (e.g., osteophytes removed). The expandable trial may be used to expand the gap in the knee during the range of motion test. For example, the expandable trial may be used to reduce laxity or maintain stability in the knee during the range of motion test.

Figure 2:
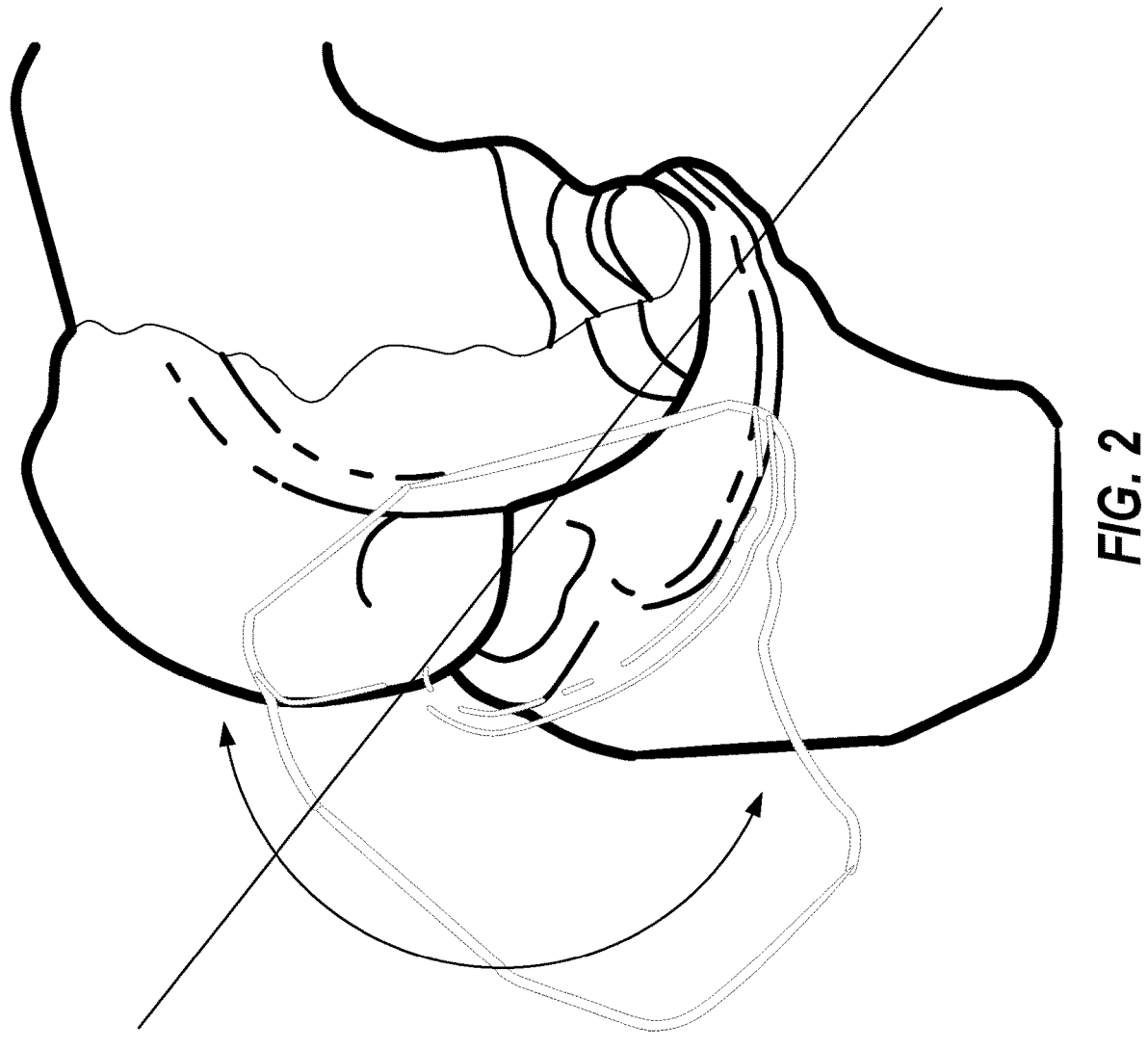
FIG. 2 illustrates the helical axis as it changes throughout a range of motion of a knee in accordance with some embodiments.

FIG. 2 illustrates the helical axis as it changes throughout a range of motion of a knee in accordance with some embodiments. FIG. 2 shows a tibia and a femur of a knee to illustrate a helical axis as it changes throughout a range of motion of the knee. For example, as the knee is moved through the range of motion, the helical axis is established as shown for movement of the tibia and the femur relative to each other or relative to soft tissue of the knee. The helical axis may be used as described herein to determine a tibial cut location, a trial size or location, an implant size or location, or the like. The range of motion evaluation (with the helical axis as shown in FIG. 2) may be performed after removal of osteophytes from the tibia.

In the example shown in FIG. 2, the tibia is moved during the range of motion test. The helical axis, along with other information obtained during, before, or after a procedure (e.g., 3D plan, resection locations, implant or trial size or location, outcome information, or the like) may be saved. The saved information may be aggregated with other information from other procedures to generate a database of procedure information. The database of procedure information may be used to train a machine learning engine as described below.

The helical axis represents a rotational axis for the knee. In an example with 0 degrees varus/valgus in the knee, and medial and lateral gaps are the same, gaps across the entire range of motion may be monitored. The results may include a visual prism (e.g., rectangular, trapezoidal, etc.) formed from measurements taken during the range of motion. For example, a series of rectangles or trapezoids (e.g., deformed across the range of motion) may be used. The output of the measurements from flexion to extension of the knee may be include a map of the range of motion (e.g., a visual representation of a trial or implant, such as a rectangle or trapezoid for each location measured during the range of motion, a smoothed map, or the like). In an example, an implant size, position, or orientation for each implant component may be output (or selected by a surgeon) to minimize error from an ideal rectangle or trapezoid across the range of motion. Other gap sizes or shapes may be used or output as well.

Figure 3A:
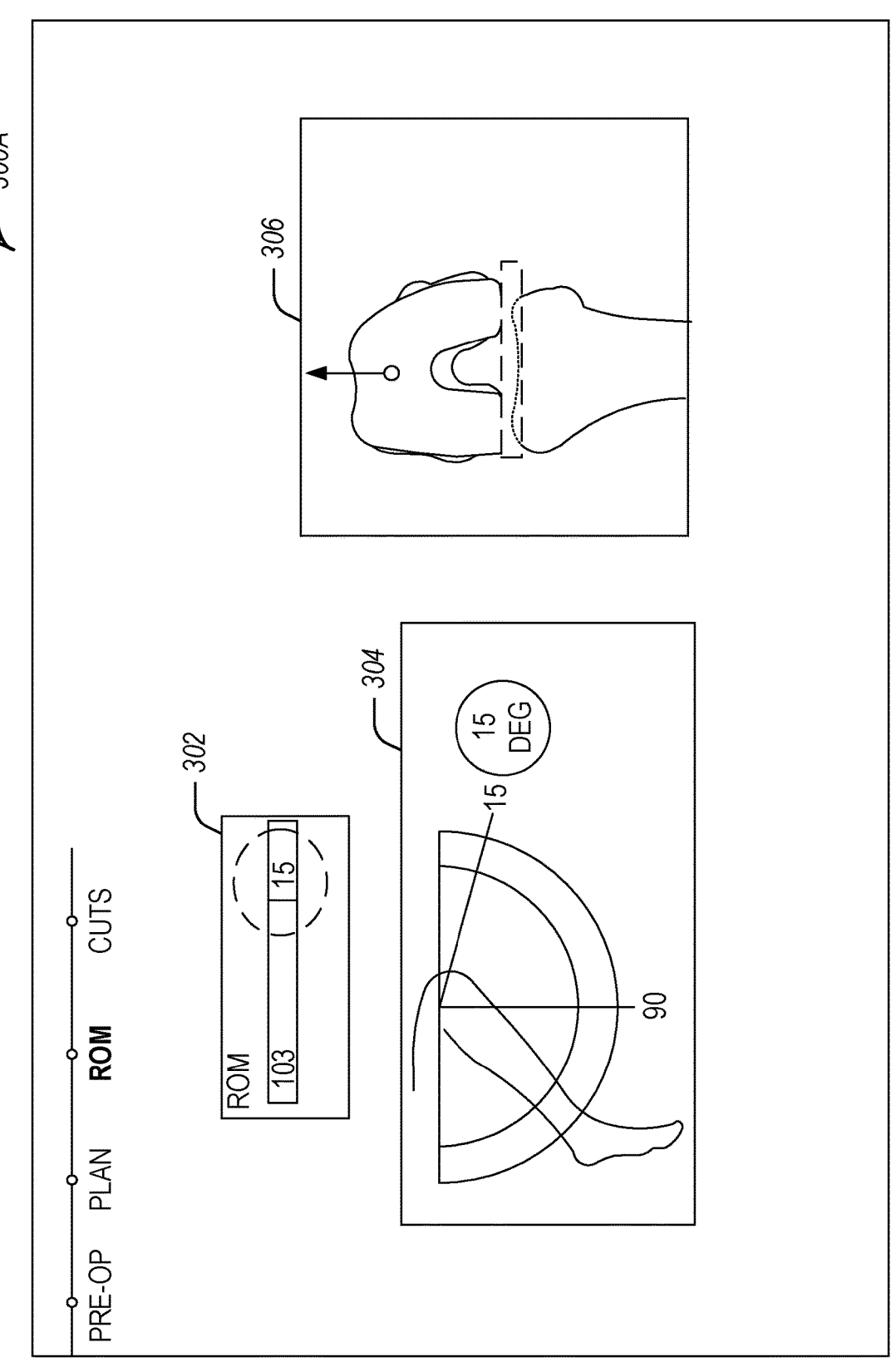
FIG. 3A illustrates a user interface for controlling a robotic device or displaying results of a range of motion test in accordance with some embodiments.

FIG. 3A illustrates a user interface 300A for controlling a robotic device or displaying results of a range of motion test in accordance with some embodiments. The user interface 300A includes a range of motion indicator 302, which may be used to display a current degree of rotation throughout the range of motion, a total range of motion for the knee, or the like. The user interface 300A may include a visualization 304 of the knee throughout the range of motion.

The user interface 300A may include a model 306 of the knee, which may include a virtual representation (or actual image) of aspects of the knee, such as a femur or tibia, or soft tissue. The model 306 may include a representation of a trial or implant, such as determined from a range of motion test as described herein. The tibia is shown in the model 306 with osteophytes removed, but a resection not yet completed. A recommended location for the tibial resection may be shown in the model 306 view on the user interface 300A, for example after a portion of the range of motion test is completed. The trial or implant or the tibial resection location may change as the range of motion test is conducted or completed.

In an example, the user interface 300A may be used to output a tibial cut recommendation (which may take into account a previous plan, ligament laxity, change in femoral component optimization versus real world placement, or the like). The original plan may be modified to make up for cartilage loss when outputting a tibial cut placement.

In an example, the user interface 300A may display measurements taken during the range of motion tests. The tibial resection location or a cut plane may be displayed in the model 306. In an example, aspects or information about kinematic alignment of the knee may be displayed on the user interface 300A. The user interface 300A may display an average of a rectangular or a trapezoidal gap, which may be used to determine a size, position, or orientation for an implant or a trial. The average of the gap may be displayed along a helical axis for placement of a femoral component. In an example, the user interface 300A displays a maximum or average medial or lateral gap distance at various points along range of motion, or a smoothed version of the maximum or average medial or lateral gap distance throughout the range of motion.

Figure 3B:
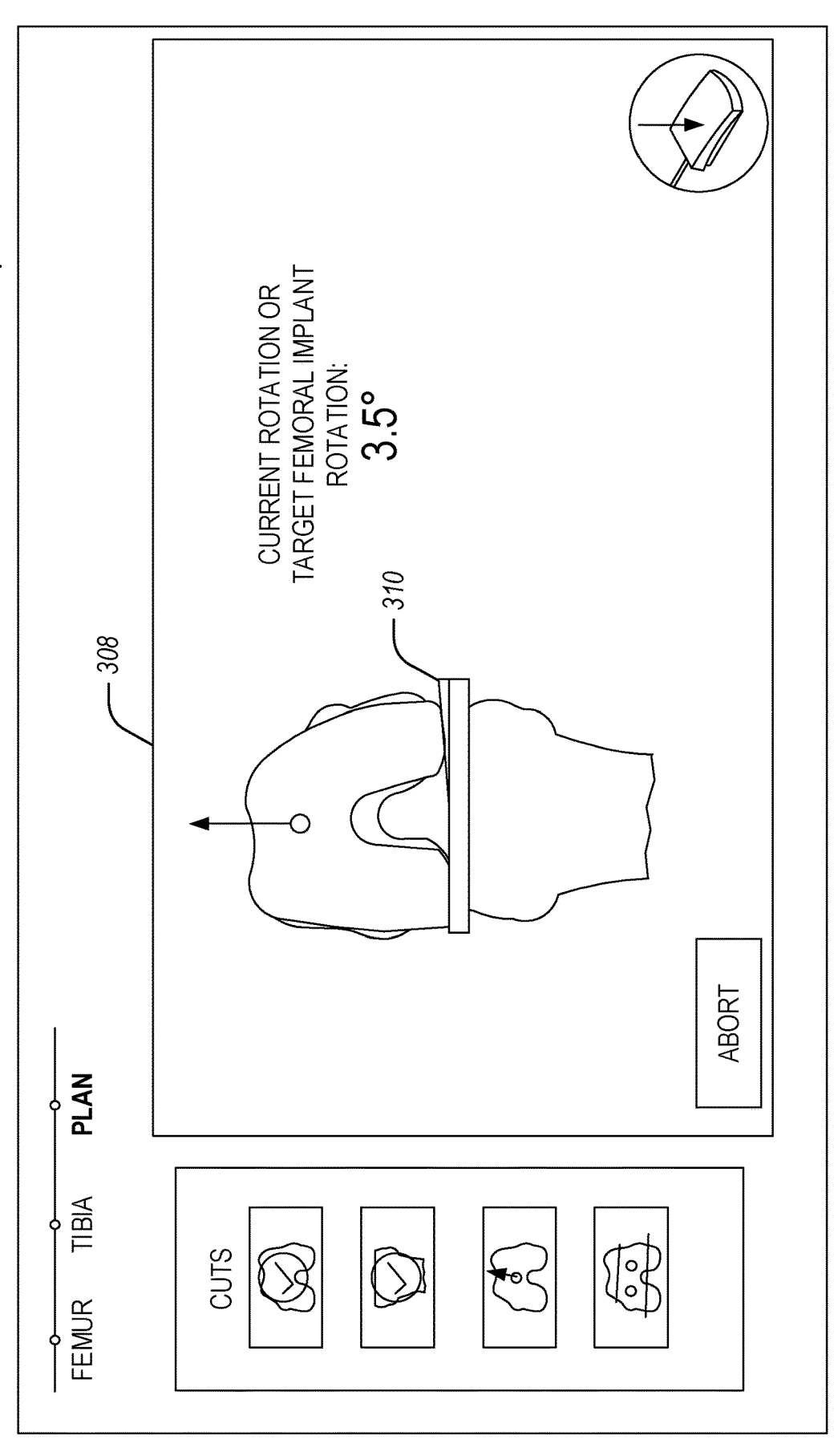
FIG. 3B illustrates an example soft-tissue trapezoidal graphic in accordance with some embodiments.

FIG. 3B illustrates an example soft-tissue trapezoidal graphic 310 in accordance with some embodiments. FIG. 3B includes a user interface 300B including a component 308 for displaying the trapezoidal graphic 310. In this example, the trapezoidal graphic 310 may display information, such as a joint gap lateral overlap or medial overlap indicator. The lateral overlap or the medial overlap indicator in this example are angled (e.g., creating a trapezoid shape). In an example, medial or lateral laxity may be displayed, including an indication of loose, neutral, or tight, as well as total laxity measurements and measures of tightness or looseness.

Figure 4:
FIG. 4 illustrates a robotic device for performing techniques described herein, in accordance with some embodiments.

FIG. 4 illustrates a robotic device for performing techniques described herein, in accordance with some embodiments. The robotic device may be used to perform a range of motion test. For example, the robotic device may be used in a sensor only mode, to collect measurements about the knee during the range of motion test (e.g., location information). The robotic device may be used in a force assist mode (which may also collect sensor information). The force assist mode may amplify force applied by a surgeon to move the knee through the range of motion. The robotic device may be used in an autonomous mode. The autonomous mode may be initiated by a surgeon, after which the robotic device may move the knee throughout the range of motion (and may collect sensor information). In an example, location information may be determined using an optical tracking system, which may be coordinated with the robotic device.

In an example, the robotic device may be used to identify an axis that the knee rotates through. The robotic device may determine anterior, distal, or posterior landmarks of the femur or the proximal tibial plateau points (e.g., during a registration phase, from preoperative imaging, from an optical tracking system in communication with the robotic device, or the like). Using a landmark, the robotic device may identify a helical axis as the knee is moved from extension to full flexion and back to extension. After the axis is identified, bony cuts of the femur or tibia may be made in parallel to the axis (e.g., as the axis changes throughout the range of motion). The axis may not be a straight line from one condyle to the next like the transepicondylar Axis, but instead may change projection as the knee goes through the range of motion. Thus the cuts of the femur or tibia may not be a straight line or plane either.

Figure 5:
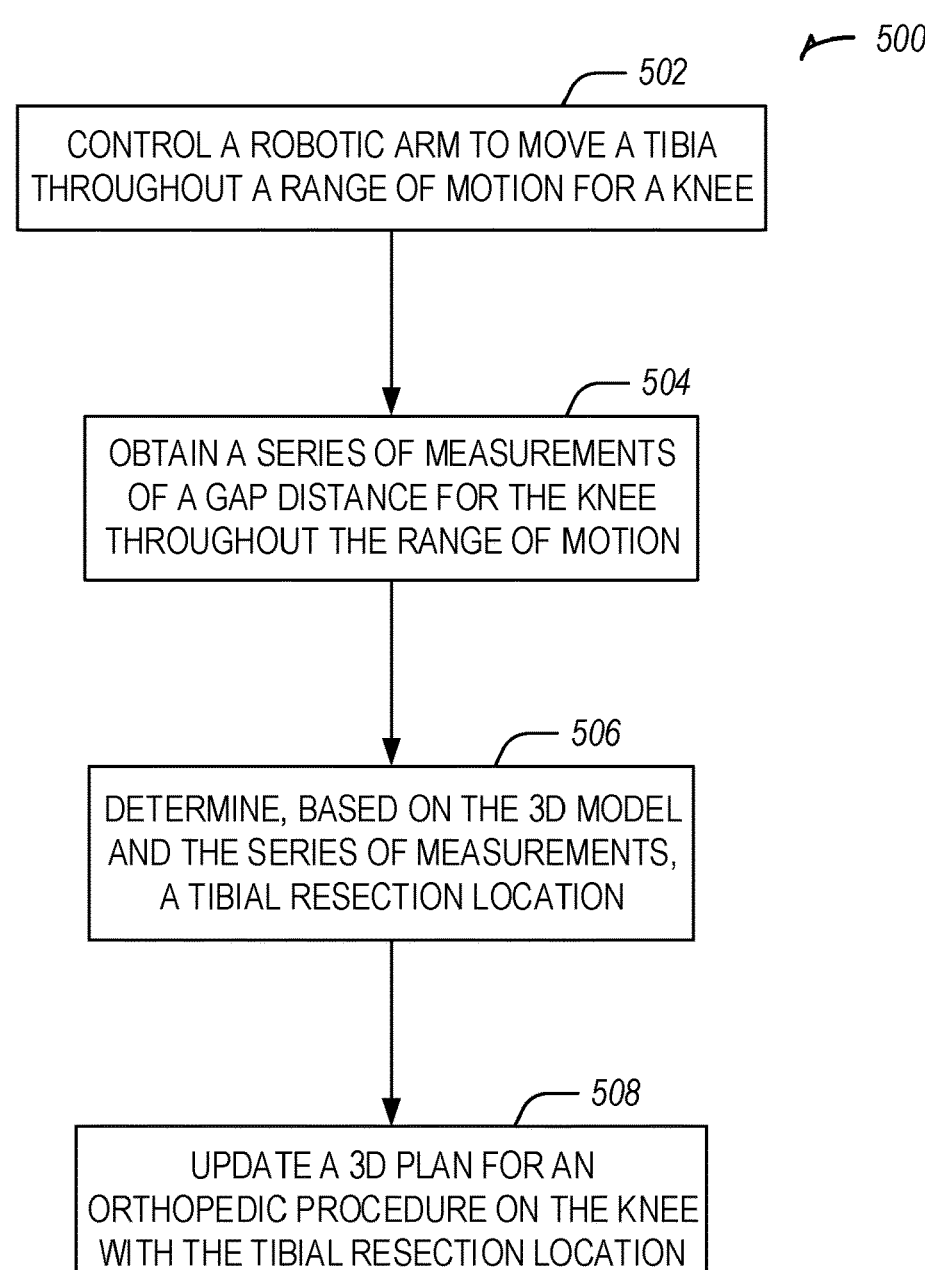
FIG. 5 illustrates a flowchart showing a technique for evaluating kinematic alignment using a robotic surgical device for a surgical knee procedure in accordance with some embodiments.

FIG. 5 illustrates a flowchart showing a technique 500 for evaluating kinematic alignment using a robotic surgical device for a surgical knee procedure in accordance with some embodiments. The technique 500 may be performed using a processor, such as a processor of a robotic surgical system to perform the following operations. In an example, a robotic controller is used to perform the following operations. The robotic controller may include the processor or the processor may include the robotic controller.

The technique 500 includes an operation 502 to control a robotic arm to move a tibia throughout a range of motion for a knee. In an example, operation 502 includes moving the robotic arm using force assist from the robotic arm. In another example, operation 502 includes sending an instruction to the robotic arm to move the tibia automatically and without surgeon interaction.

The technique 500 includes an operation 504 to obtain a series of measurements of a gap distance for the knee throughout the range of motion. Operation 504 may include using position data of the robotic arm to evaluate the gap distance for the knee throughout the range of motion. For example, the position data may be derived from a robotic coordinate system.

The technique 500 includes an operation 506 to determine, based on the 3D model and the series of measurements, a tibial resection location. Operation 506 may include determining a tibial cut plane such that after the tibia is resected and an implant is inserted, the gap distance between a femur and the tibia of the knee is minimized throughout the range of motion. Minimizing the gap distance may include minimizing an overall gap distance, a medial gap distance, a lateral gap distance, or the like. The technique 500 may be used to minimize error from an ideal rectangle or trapezoid to the gap distance across the range of motion.

In an example, operation 506 includes using the series of measurements as an input to a machine learning engine. The machine learning engine may be trained using prior gap distance measurements and outcome information (e.g., from previous range of motion tests, which may have been performed by a robotic arm or manually). The machine learning engine may output the tibial resection location. For a particular patient, prior gap distance measurements from a prior surgery on the non-operative knee (e.g., the other side, right or left) can be used to plan the mechanics and balancing of the operative knee if the outcome information indicates a favorable outcome from the prior surgery on the non-operative knee.

The technique 500 includes an operation 508 to update a 3D plan for an orthopedic procedure on the knee with the tibial resection location. In an example, operation 508 includes generating a range of motion gap distance model based on the series of measurements, including a medial gap distance and a lateral gap distance at three or more locations along the range of motion. In this example, the three or more locations may occur every degree throughout the range of motion. The operation 508 may include updating a planned implant based on the series of measurements. For example, updating the planned implant may include generating an implant shape based on a maximum medial gap distance and a maximum lateral gap distance in the series of measurements.

In an example, operation 508 may include planning a resection to result in a gap profile that most closely matches the gap profile determined by the range of motion assessment. The determination of what matches best may be done by averaging the gaps or by the error minimization process. In an example, a trapezoidal implant may be used to leave a slightly greater gap on one side (e.g., medial or lateral) purposefully.

The technique 500 may include preoperatively generating a 3D plan for an orthopedic procedure on the knee before controlling the robotic arm to move the tibia throughout the range of motion. The technique 500 may include an operation to remove osteophytes from the tibia of the knee before controlling the robotic arm to move the tibia throughout the range of motion. The technique 500 may include generating information indicative of an axis through a femur of the knee.

Figure 6:
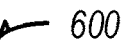
FIG. 6 illustrates a system for performing techniques described herein, in accordance with some embodiments.

FIG. 6 illustrates a robotic surgical system 600 for performing techniques described herein, in accordance with some embodiments. The robotic surgical system 600 includes a robotic surgical arm 602 including a sensor 604. The sensor 604 may include an accelerometer, gyroscope, or other sensor, any of which may be used to determine a location of a portion of the robotic surgical arm 602. The sensor may output measurements, such as a series of measurements throughout a range of motion of a knee as the robotic surgical arm 602 moves a tibia of the knee.

The robotic surgical arm 602 may include a motor, such as for autonomous movement or for use in as a force assist. The motor may be used to conduct the range of motion test.

A control system 618 (e.g., a robotic controller), may include a processor 620 and memory 622. The control system 618 may be a part of the robotic surgical arm 602 or may be communicatively coupled to the robotic surgical arm 602. The processor 602 may be used to perform the technique 500 or operations thereof.

A display device 614 may be a part of the robotic surgical arm 602 or may be communicatively coupled to the robotic surgical arm 602. The display device 614 may be used to display a user interface 616.

In an example, the display device 1614 may be used to display results (e.g., measurements, a tibial resection location, a cut plane, a recommended trial or implant, etc.) of a range of motion test on the user interface 616. The results may include gap distance information, such as at different angles during a range of motion test. The gap distance information may be derived from a sensor, such as a sensor 604, which may be on the robotic surgical arm 602.

Figure 7:
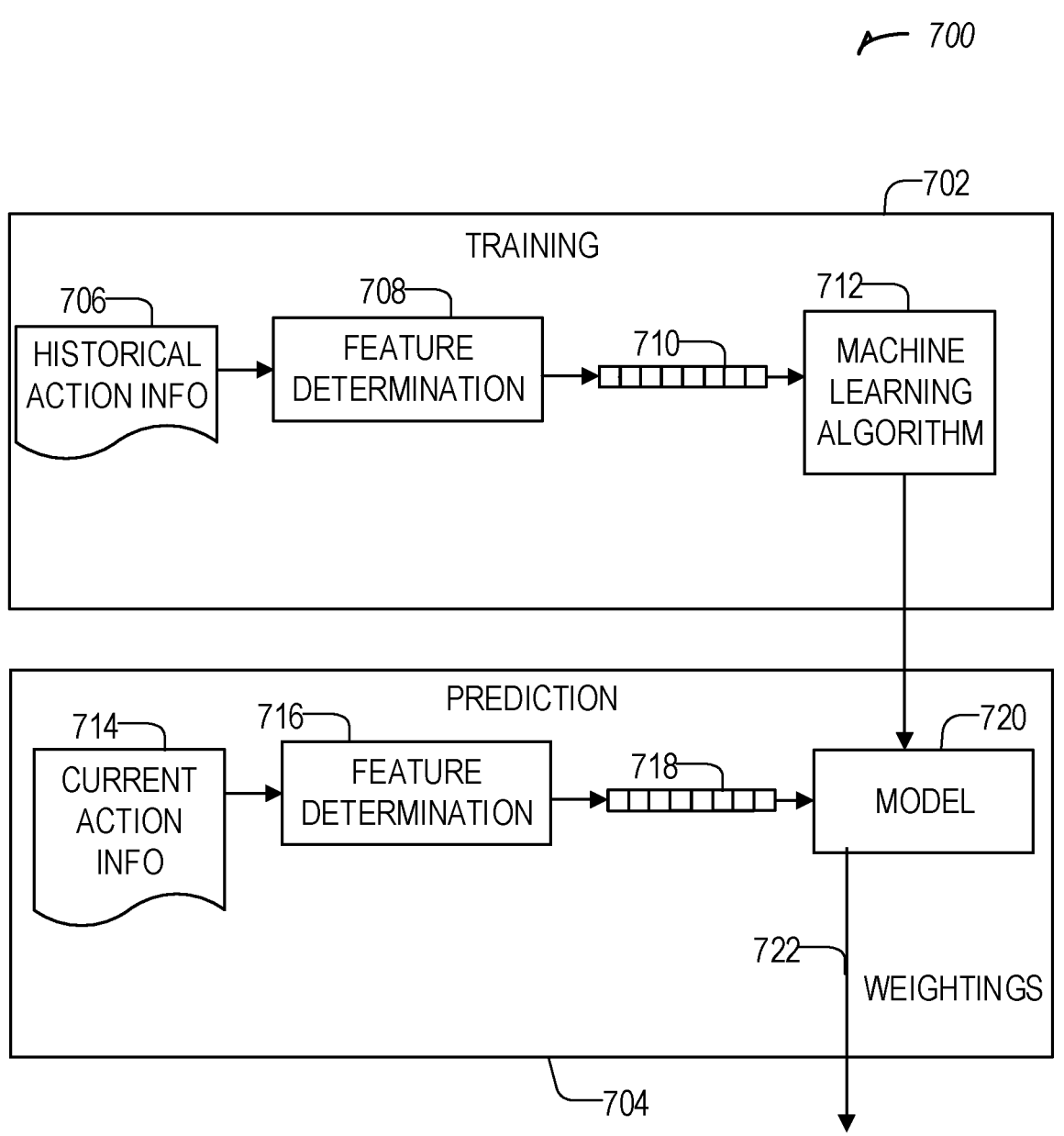
FIG. 7 illustrates a machine learning engine for evaluating range of motion data to aid in knee arthroplasty and other surgical procedures in accordance with some embodiments.

FIG. 7 illustrates a machine learning engine for evaluating range of motion data to aid in knee arthroplasty and other surgical procedures in accordance with some embodiments. A system may calculate one or more weightings for criteria based upon one or more machine learning algorithms. FIG. 7 shows an example machine learning engine 700 according to some examples of the present disclosure. Machine learning engine 700 may be part of the system 600 of FIG. 6, for example implemented using a database, a server, etc., or the like.

Machine learning engine 700 utilizes a training engine 702 and a prediction engine 704. Training engine 702 inputs historical transaction information 706 for historical actions of stored or generated at a robotic surgical device, for example, into feature determination engine 708. The historical action information 706 may be labeled with an indication, such as a degree of success of an outcome of a surgical procedure, which may include pain information, patient feedback, implant success, ambulatory information, or the like. In some examples, an outcome may be subjectively assigned to historical data, but in other examples, one or more labelling criteria may be utilized that may focus on objective outcome metrics (e.g., pain rating, survey score, a patient satisfaction score, such as a forgotten knee score, a Western Ontario and McMaster Universities Osteoarthritis Index (WOMAC) score, or the like).

Feature determination engine 708 determines one or more features 710 from this historical information 706. Stated generally, features 710 are a set of the information input and is information determined to be predictive of a particular outcome. Example features are given above. In some examples, the features 710 may be all the historical activity data, but in other examples, the features 710 may be a subset of the historical activity data. The machine learning algorithm 712 produces a model 720 based upon the features 710 and the labels. The historical action information 706 may include a gap distance within the knee of the patient, a varus/valgus angle, other aspects of soft tissue or alignment of the knee, an axis through the distal femur, a position of a femoral component, a tibial cut location, a shape of an implant, or the like. The historical action information 706 may include measurements taken, for example, at degree, half degree, or quarter degree increments along a range of motion.

In the prediction engine 704, current action information 714 (e.g., a surgical plan, an action to be taken or a last action taken, such as by a robotic surgical device, or the like) may be input to the feature determination engine 716. Feature determination engine 716 may determine the same set of features or a different set of features from the current information 714 as feature determination engine 708 determined from historical information 706. In some examples, feature determination engine 716 and 708 are the same engine. Feature determination engine 716 produces feature vector 718, which is input into the model 720 to generate one or more criteria weightings 722. The training engine 702 may operate in an offline manner to train the model 720. The prediction engine 704, however, may be designed to operate in an online manner. In an example, the model 720 may be periodically updated via additional training or user feedback (e.g., an update to a technique or procedure).

The machine learning algorithm 712 may be selected from among many different potential supervised or unsupervised machine learning algorithms. Examples of supervised learning algorithms include artificial neural networks, Bayesian networks, instance-based learning, support vector machines, decision trees (e.g., Iterative Dichotomiser 3, C4.5, Classification and Regression Tree (CART), Chi-squared Automatic Interaction Detector (CHAID), and the like), random forests, linear classifiers, quadratic classifiers, k-nearest neighbor, linear regression, logistic regression, and hidden Markov models. Examples of unsupervised learning algorithms include expectation-maximization algorithms, vector quantization, and information bottleneck method. Unsupervised models may not have a training engine 702. In an example embodiment, a regression model is used and the model 720 is a vector of coefficients corresponding to a learned importance for each of the features in the vector of features 710, 718.

Figure 8:
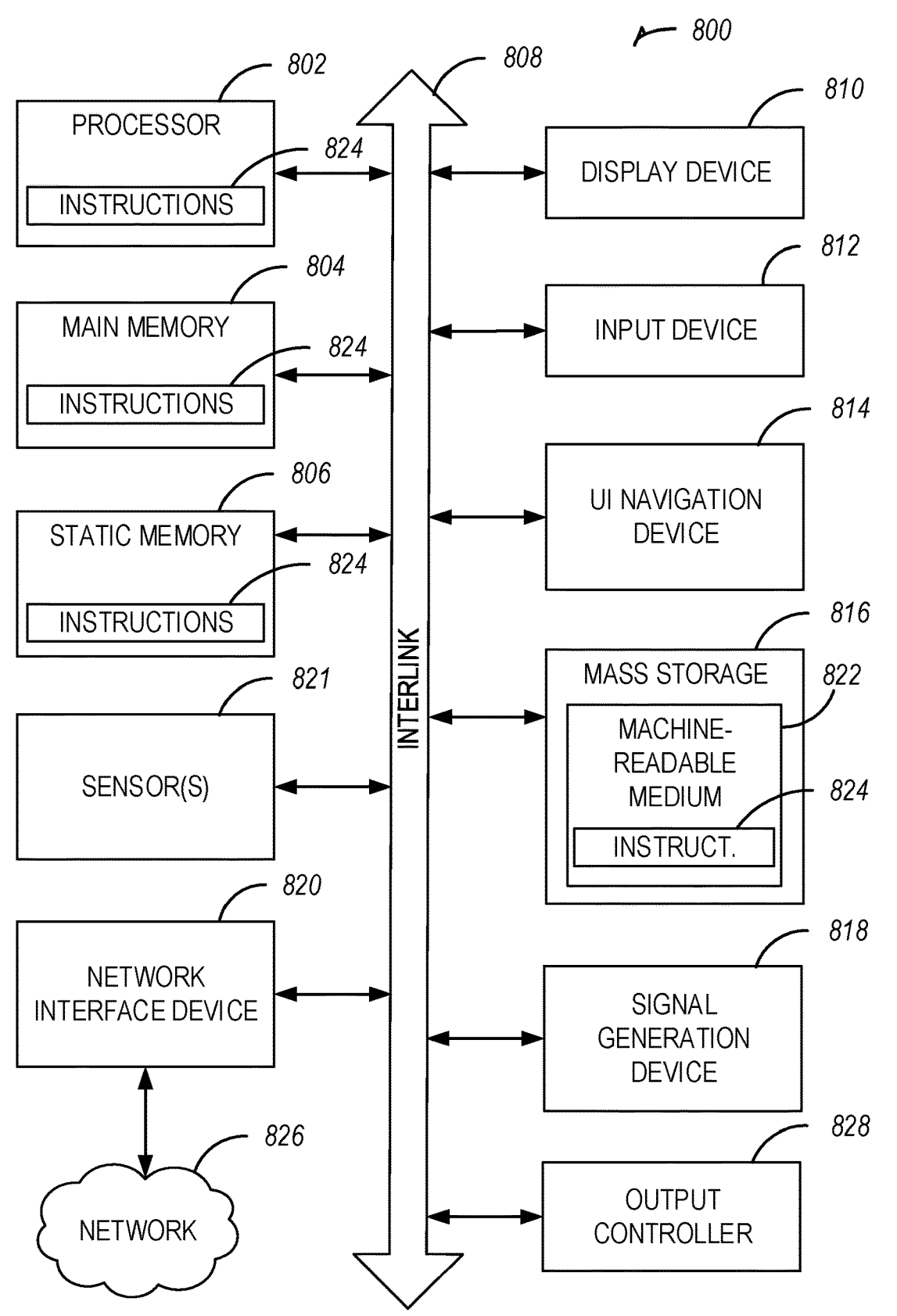
FIG. 8 illustrates a block diagram of an example of a machine upon which any one or more of the techniques discussed herein may perform in accordance with some embodiments.

FIG. 8 illustrates a block diagram of an example machine 800 upon which any one or more of the techniques discussed herein may perform in accordance with some embodiments. In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810, an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensor. The machine 800 may include an output controller 828, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine readable media.

While the machine readable medium 822 is illustrated as a single medium, the term "machine readable medium" may include a single medium or multiple media (e.g., a centralized or distributed database, and/or associated caches and servers) configured to store the one or more instructions 824. The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 824 may further be transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Each of these non-limiting examples may stand on its own, or may be combined in various permutations or combinations with one or more of the other examples.

Example 1 is a robotic surgical system comprising: a robotic controller to control a robotic arm to move a tibia throughout a range of motion for a knee; a sensor to obtaining a series of measurements of a gap distance for the knee throughout the range of motion; and a processor to: determine, based on a 3D model and the series of measurements, a tibial resection location; and update a 3D plan for an orthopedic procedure on the knee with the tibial resection location.

In Example 2, the subject matter of Example 1 includes, wherein the processor is further to preoperatively generate the 3D plan for an orthopedic procedure on the knee before controlling the robotic arm to move the tibia throughout the range of motion.

In Example 3, the subject matter of Examples 1-2 includes, wherein the robotic controller is further to cause the robotic arm to remove osteophytes from the tibia of the knee before controlling the robotic arm to move the tibia throughout the range of motion.

In Example 4, the subject matter of Examples 1-3 includes, wherein the processor is further to generate information indicative of an axis through a femur of the knee.

In Example 5, the subject matter of Examples 1-4 includes, wherein to update the 3D plan, the processor is further to generate a range of motion gap distance model based on the series of measurements, including a medial gap distance and a lateral gap distance at three or more locations along the range of motion.

In Example 6, the subject matter of Example 5 includes, wherein the three or more locations occur every degree throughout the range of motion.

In Example 7, the subject matter of Examples 1-6 includes, wherein the tibial resection location is a tibial cut plane determined such that after the tibia is resected and an implant is inserted, the gap distance between a femur and the tibia of the knee is minimized throughout the range of motion.

In Example 8, the subject matter of Examples 1-7 includes, wherein to update the 3D plan, the processor is further to update a planned implant based on the series of measurements.

In Example 9, the subject matter of Example 8 includes, wherein to update the planned implant, the processor is further to determine a minimum error from an ideal rectangle or trapezoid to the gap distance across the range of motion.

In Example 10, the subject matter of Examples 1-9 includes, wherein to determine the tibial resection location, the processor is further to use the series of measurements as an input to a machine learning engine, the machine learning engine trained using prior gap distance measurements and outcome information, and receive the tibial resection location as an output of the machine learning engine.

In Example 11, the subject matter of Examples 1-10 includes, wherein to obtain the series of measurements, the sensor is configured to determine position data for the robotic arm, and wherein the processor is to use the position data to evaluate the gap distance for the knee throughout the range of motion.

In Example 12, the subject matter of Example 11 includes, wherein to control the robotic arm to move the tibia throughout the range of motion, the robotic controller is further to activate a force assist for the robotic arm.

In Example 13, the subject matter of Examples 11-12 includes, wherein to control the robotic arm to move the tibia throughout the range of motion, the robotic controller is to cause the robotic arm to move the tibia automatically and without surgeon interaction.

Example 14 is a method comprising: using a processor of a robotic surgical system to perform operations comprising: controlling a robotic arm to move a tibia throughout a range of motion for a knee; obtaining a series of measurements of a gap distance for the knee throughout the range of motion; determining, based on a 3D model and the series of measurements, a tibial resection location; and updating a 3D plan for an orthopedic procedure on the knee with the tibial resection location.

In Example 15, the subject matter of Example 14 includes, preoperatively generating a 3D plan for an orthopedic procedure on the knee before controlling the robotic arm to move the tibia throughout the range of motion.

In Example 16, the subject matter of Examples 14-15 includes, removing osteophytes from the tibia of the knee before controlling the robotic arm to move the tibia throughout the range of motion.

In Example 17, the subject matter of Examples 14-16 includes, generating information indicative of an axis through a femur of the knee.

In Example 18, the subject matter of Examples 14-17 includes, wherein updating the 3D plan includes generating a range of motion gap distance model based on the series of measurements, including a medial gap distance and a lateral gap distance at three or more locations along the range of motion.

In Example 19, the subject matter of Example 18 includes, wherein the three or more locations occur every degree throughout the range of motion.

In Example 20, the subject matter of Examples 14-19 includes, wherein determining the tibial resection location includes determining a tibial cut plane such that after the tibia is resected and an implant is inserted, the gap distance between a femur and the tibia of the knee is minimized throughout the range of motion.

In Example 21, the subject matter of Examples 14-20 includes, wherein updating the 3D plan includes updating a planned implant based on the series of measurements.

In Example 22, the subject matter of Example 21 includes, wherein updating the planned implant includes determining a minimum error from an ideal rectangle or trapezoid to the gap distance across the range of motion.

In Example 23, the subject matter of Examples 14-22 includes, wherein determining the tibial resection location includes using the series of measurements as an input to a machine learning engine, trained using prior gap distance measurements and outcome information, and receiving the tibial resection location as an output of the machine learning engine.

In Example 24, the subject matter of Examples 14-23 includes, wherein obtaining the series of measurements includes using position data of the robotic arm to evaluate the gap distance for the knee throughout the range of motion.

In Example 25, the subject matter of Example 24 includes, wherein controlling the robotic arm to move the tibia throughout the range of motion includes moving the robotic arm using force assist from the robotic arm.

In Example 26, the subject matter of Examples 24-25 includes, wherein controlling the robotic arm to move the tibia throughout the range of motion includes sending an instruction to the robotic arm to move the tibia automatically and without surgeon interaction.

Example 27 is a machine-readable medium including instructions, which when executed by a processor, cause the processor to perform operations to: control a robotic arm to move a tibia throughout a range of motion for a knee; obtain a series of measurements of a gap distance for the knee throughout the range of motion; determine, based on the 3D model and the series of measurements, a tibial resection location; and update a 3D plan for an orthopedic procedure on the knee with the tibial resection location.

In Example 28, the subject matter of Example 27 includes, instructions to cause the processor to preoperatively generate a 3D plan for an orthopedic procedure on the knee before controlling the robotic arm to move the tibia throughout the range of motion.

In Example 29, the subject matter of Examples 27-28 includes, instructions to cause the robotic arm to remove osteophytes from the tibia of the knee before controlling the robotic arm to move the tibia throughout the range of motion.

In Example 30, the subject matter of Examples 27-29 includes, instructions to cause the processor to generate information indicative of an axis through a femur of the knee.

In Example 31, the subject matter of Examples 27-30 includes, wherein the instructions to update the 3D plan include instructions that cause the processor to generate a range of motion gap distance model based on the series of measurements, including a medial gap distance and a lateral gap distance at three or more locations along the range of motion.

In Example 32, the subject matter of Example 31 includes, wherein the three or more locations occur every degree throughout the range of motion.

In Example 33, the subject matter of Examples 27-32 includes, wherein the instructions to determine the tibial resection location include instructions that cause the processor to determine a tibial cut plane such that after the tibia is resected and an implant is inserted, the gap distance between a femur and the tibia of the knee is minimized throughout the range of motion.

In Example 34, the subject matter of Examples 27-33 includes, wherein the instructions to update the 3D plan include instructions that cause the processor to update a planned implant based on the series of measurements.

In Example 35, the subject matter of Example 34 includes, wherein the instructions to update the planned implant include instructions that cause the processor to determine a minimum error from an ideal rectangle or trapezoid to the gap distance across the range of motion.

In Example 36, the subject matter of Examples 27-35 includes, wherein the instructions to determine the tibial resection location include instructions that cause the processor to use the series of measurements as an input to a machine learning engine, trained using prior gap distance measurements and outcome information, and receiving the tibial resection location as an output of the machine learning engine.

In Example 37, the subject matter of Examples 27-36 includes, wherein the instructions to obtain the series of measurements include instructions that cause the processor to use position data of the robotic arm to evaluate the gap distance for the knee throughout the range of motion.

In Example 38, the subject matter of Example 37 includes, wherein the instructions to control the robotic arm to move the tibia throughout the range of motion include instructions that cause the processor to move the robotic arm using force assist from the robotic arm.

In Example 39, the subject matter of Examples 37-38 includes, wherein the instructions to control the robotic arm to move the tibia throughout the range of motion include instructions that cause the processor to send an instruction to the robotic arm to move the tibia automatically and without surgeon interaction.

Example 40 is at least one machine-readable medium including instructions that, when executed by processing circuitry, cause the processing circuitry to perform operations to implement of any of Examples 1-39.

Example 41 is an apparatus comprising means to implement of any of Examples 1-39.

Example 42 is a system to implement of any of Examples 1-39.

Example 43 is a method to implement of any of Examples 1-39.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A non-transitory machine-readable medium including instructions, which when executed by processing circuitry, cause the processing circuitry to perform operations to:

transmit control signals to a robotic arm of a robotic surgical system, the control signals configured to control the robotic arm to move a tibia throughout a range of motion for a knee;

obtain, from a sensor operably coupled to the robotic arm, at least one measurement of a gap distance for the knee at a location in the range of motion;

determine, based on a model of the knee and the at least one measurement, a change to an implant size;

update a plan for an orthopedic procedure on the knee with the change to the implant size; and control the robotic arm to move based on the updated plan.

2. The non-transitory machine-readable medium of claim 1, further comprising instructions to cause the processing circuitry to preoperatively generate the plan for an orthopedic procedure on the knee before controlling the robotic arm to move the tibia throughout the range of motion.

3. The non-transitory machine-readable medium of claim 1, wherein the instructions to determine the change to the implant size include instructions that cause the processing circuitry to use the at least one measurement as an input to a machine learning engine, trained using prior sizing measurements and outcome information, and receiving the change to the implant size as an output of the machine learning engine.

4. A robotic surgical system comprising:

a robotic controller to control a robotic arm to move a tibia throughout a range of motion for a knee;

a sensor to obtain at least one measurement of a gap distance for the knee at a location in the range of motion;

processing circuitry; and a machine-readable medium including instructions, which when executed by the processing circuitry, cause the processing circuitry to perform operations to:

transmit control signals to the robotic arm of the robotic surgical system, the control signals configured to control the robotic arm via the robotic controller to move the tibia throughout the range of motion for the knee;

obtain, from the sensor operably coupled to the robotic arm, the at least one measurement of the gap distance for the knee at the location in the range of motion from the sensor;

determine, based on a model of the knee and the at least one measurement, a change to an implant size;

update a plan for an orthopedic procedure on the knee with the change to the implant size; and control the robotic arm to move based on the updated plan.

5. The robotic surgical system of claim 4, wherein the processing circuitry is further to preoperatively generate the plan for an orthopedic procedure on the knee before controlling the robotic arm to move the tibia throughout the range of motion.

6. The robotic surgical system of claim 4, wherein the robotic controller is further to cause the robotic arm to remove osteophytes from the tibia of the knee before controlling the robotic arm to move the tibia throughout the range of motion.

7. The robotic surgical system of claim 4, wherein the processing circuitry is further to generate information indicative of an axis through a femur of the knee.

8. The robotic surgical system of claim 4, wherein to update the plan, the processing circuitry is further to generate a range of motion gap distance model based on the at least one measurement, including a medial gap distance and a lateral gap distance at a location along the range of motion.

9. The robotic surgical system of claim 4, wherein to update the plan, the processing circuitry is further to generate a range of motion gap distance model based on the at least one measurement, including medial gap distances and lateral gap distances at every degree throughout the range of motion.

10. The robotic surgical system of claim 4, wherein a planned laxity is adjusted based on the change to the implant size.

11. The robotic surgical system of claim 4, wherein to update the plan, the processing circuitry is further to update a tibial resection location based on the at least one measurement.

12. The robotic surgical system of claim 4, wherein to update the plan with the change to the implant size, the processing circuitry is further to determine a minimum error from an ideal rectangle or trapezoid to the gap distance across the range of motion.

13. The robotic surgical system of claim 4, wherein to determine the change to the implant size, the processing circuitry is further to use the at least one measurement as an input to a machine learning engine, the machine learning engine trained using prior sizing measurements and outcome information, and receive the change to the implant size as an output of the machine learning engine.

14. The robotic surgical system of claim 4, wherein to obtain the at least one measurement, the sensor is configured to determine position data for the robotic arm, and wherein the processing circuitry is to use the position data to evaluate the gap distance for the knee throughout the range of motion.

15. The robotic surgical system of claim 4, wherein to control the robotic arm to move the tibia throughout the range of motion, the robotic controller is further to activate a force assist for the robotic arm.

16. The robotic surgical system of claim 4, wherein to control the robotic arm to move the tibia throughout the range of motion, the robotic controller is to cause the robotic arm to move the tibia automatically and without surgeon interaction.

17. A method comprising:

transmitting, using processing circuitry of a robotic surgical system, control signals to a robotic arm of the robotic surgical system, the control signals configured to control the robotic arm to move a tibia throughout a range of motion for a knee;

obtaining, from a sensor operably coupled to the robotic arm and using the processing circuitry of the robotic surgical system, at least one measurement of a gap distance for the knee at a location in the range of motion;

determining, using the processing circuitry of the robotic surgical system, based on a model of the knee and the at least one measurement, a change to an implant size;

updating, using the processing circuitry of the robotic surgical system, a plan for an orthopedic procedure on the knee with the change to the implant size; and controlling the robotic arm to move based on the updated plan.

18. The method of claim 17, further comprising preoperatively generating, using the processing circuitry of the robotic surgical system, a plan for an orthopedic procedure on the knee before controlling the robotic arm to move the tibia throughout the range of motion.

19. The method of claim 17, wherein updating the plan includes generating, using the processing circuitry of the robotic surgical system, a range of motion gap distance model based on the at least one measurement, including a medial gap distance and a lateral gap distance at three or more locations along the range of motion.

20. The method of claim 17, further comprising adjusting, using the processing circuitry of the robotic surgical system, a planned laxity based on the change to the implant size.

\* \* \* \* \*